United States Patent [19]
Loeb

[11] Patent Number: 5,833,714
[45] Date of Patent: Nov. 10, 1998

[54] COCHLEAR ELECTRODE ARRAY EMPLOYING TANTALUM METAL

[76] Inventor: Gerald E. Loeb, 90 Bagot Street, Kingston, Ontario, Canada, K7L 3E5

[21] Appl. No.: 784,209

[22] Filed: Jan. 15, 1997

Related U.S. Application Data

[60] Provisional application No. 60/010,156 Jan. 18, 1996.
[51] Int. Cl.$^6$ ...................................................... A61N 1/04
[52] U.S. Cl. ............................................. 607/56; 607/137
[58] Field of Search ............................... 607/55–57, 136, 607/137, 115, 116

[56] References Cited

U.S. PATENT DOCUMENTS

| | | |
|---|---|---|
| 3,646,940 | 3/1972 | Timm et al. . |
| 4,006,748 | 2/1977 | Schulman . |
| 4,333,072 | 6/1982 | Beigel ...................................... 340/825 |
| 4,408,608 | 10/1983 | Daly et al. . |
| 4,440,178 | 4/1984 | Bussard et al. . |
| 4,494,545 | 1/1985 | Slocum et al. . |
| 4,524,774 | 6/1985 | Hildebrandt . |
| 4,532,930 | 8/1985 | Crosby et al. . |
| 4,679,560 | 7/1987 | Galbraith . |
| 4,763,656 | 8/1988 | Nauman . |
| 5,193,539 | 3/1993 | Schulman et al. . |
| 5,193,540 | 3/1993 | Schulman et al. . |
| 5,312,439 | 5/1994 | Loeb ........................................... 607/2 |
| 5,324,316 | 6/1994 | Schulman et al. ......................... 607/61 |
| 5,405,367 | 4/1995 | Schulman et al. ......................... 607/61 |
| 5,466,247 | 11/1995 | Scheiner et al. ........................... 607/48 |

OTHER PUBLICATIONS

Product Description, features and diagram of "Implantable Transponder TX1400" from Identification Devices, Inc.
"Capacitor Electrode Stimulates Nerve or Muscle without Oxidation–Reduction Reactions", Science, vol. 181, pp. 74–76.
Lagow, et al., "Anodic Insulated Tantalum Oxide Electrocardiograph Electrodes", *IEEE Transactions on Bio–Medical Engineering*, pp. 162–164 (Mar. 1971).
Guyton, et al., "Theory and Design of Capacitor Electrodes for Chronic Stimulation", *Medical and Biological Engineering*, pp. 613–619 (Sep. 1974).
White, "The Stanford Artificial Ear Project", *The Stanford Engineer*, pp. 3–10 (Spring/Summer 1980).
"CRC Critical Review in Bioengineering", pp. 77–79 (Sep. 1981).

(List continued on next page.)

*Primary Examiner*—William E. Kamm
*Assistant Examiner*—George R. Evanisko

[57] ABSTRACT

An implant device uses tantalum and tantalum pentoxide as a complete system for the conveyance of electrical stimulation pulses from stimulus-forming circuitry contained within an hermetic enclosure to the saline fluids of the cochlea (or other tissue to be stimulated). Internal coupling capacitors are not used, yet the danger of having DC current flow to the saline fluids is eliminated. A preferred embodiment is a cochlear prosthesis comprised of a multiplicity of electrode contacts made from sintered, anodized tantalum, connected via tantalum wire leads to tantalum feedthroughs into the hermetically sealed package containing the stimulus pulse-forming electronic circuitry. One or more counterelectrode contacts (for monopolar or bipolar configurations, respectively) consist of activated iridium, connected via platinum or other noble metal leads to noble metal feedthroughs. When powered-up, the stimulus generating circuit produces a steady polarizing potential of approximately half its maximum output voltage range, which potential is applied as a positive (anodizing) voltage to each tantalum electrode and associated lead and feedthrough, with respect to the activated iridium electrode(s), which act as the reference point for the circuit.

7 Claims, 4 Drawing Sheets

OTHER PUBLICATIONS

Robblee, et al., "Activated Ir: An Electrode Suitable for Reversible Charge Injection in Saline Solution", *J. Electrochem. Soc.: Accelerated Brief Communication,* vol. 130:3, pp. 731–733, (Mar. 1983).

Rose, et al., "Assessment of Capacitor Electrodes for Intracortical Neural Stimulation", *Journal of Neuroscience Methods,* vol. 12, pp. 181–193 (1985).

Kaximierczuk, et al., "Exact Analysis of Class E Tuned Power Amplifier at any Q and Switch Duty Cycle", *IEEE Transactions on Circuits and Systems,* vol. CAS–34:2, pp. 149–159 (Feb. 1987).

Loeb, et al., "Injectable Microstimulator for Functional Electrical Stimulation", *Medical and Biological Engineering and Computer,* 29:NS 13–19 (1991).

Heetderks, "RF Powering of Millimeter–and Submillimeter–Sized Neural Prosthetic Implants", *IEEE Transactions on Biomedical Engineering,* vol. 35:5, pp. 323–326 (May 1988).

COCHLEAR ELECTRODE ARRAY EMPLOYING TANTALUM METAL

This application claims priority to U.S. Provisional Application Ser. No. 60/010,156, filed 18 Jan. 1996, under 35 U.S.C. 5119 (c).

BACKGROUND OF THE INVENTION

The present invention relates to implantable stimulation devices, e.g., cochlear prostheses used to electrically stimulate the auditory nerve, and more particularly to the electrodes or electrode contacts used with such implantable stimulating devices.

Most cochlear prosthesis currently employ an array of closely spaced electrode contacts implanted in the scala tympani, where they are used to selectively stimulate multiple regions of the tonotopically arranged spiral ganglion cells, which comprise the auditory nerve. In order to minimize the electrical power required to activate the nerve cells, the impedance of the electrical load presented to the stimulating circuitry needs to be minimized. In order to avoid damage to the neurons and other surrounding tissues, the stimulation waveforms must be strictly charge-balanced; i.e., there must be no net direct current flow. In order to simplify surgical implantation and minimize danger of extrusion through the skin, the volume occupied by the electronic circuitry and any associated packaging and connections must be minimized.

In the present art, the above requirements are usually met by employing metal electrode contacts, and connecting such electrode contacts to hermetically sealed electronic circuits via leads and feedthroughs into the hermetically sealed electronic package. The electrode contacts typically consist of the noble metal platinum and its alloys with iridium. This choice gives rise to the following design problems and strategies for coping with them:

1. Provision of Biphasic Pulses

Electrical stimulation pulses having two opposite phases each with equal charge are actively applied to each contact. Sometimes such pulses are applied to one intracochlear contact with respect to an indifferent electrode usually located outside the cochlea, a configuration known as "monopolar." At other times or in other devices, such pulses may be applied bipolarly between two or more intracochlear contacts. In general, these actively driven biphasic pulses require pulse-forming circuitry to produce two different polarities of voltage and current, either by operating in a push-pull configuration with both positive and negative power supply voltages or by employing switching networks in the output stages that can reverse the direction of current flow through the electrodes to which it is intermittently connected. When such circuitry is used with more than one output circuit and/or electrode pair at a time, care must be taken to avoid inadvertently producing summation of output voltages with voltages stored on various output capacitors and electrodes that may exceed the operating voltage range of the circuitry, thereby producing unreliable function or damage. In practice, this often makes it impossible to use the full dynamic range of voltage that is actually produced or nominally tolerated by the circuitry.

2. Prevention of Net DC

Usually a capacitor is incorporated in series with each intracochlear contact to block any net DC current that might arise through slight inequalities between the two opposite phases of the stimulation pulses. One disadvantage of such capacitors is that they have a finite impedance, which is in series with the electrode impedance, and increases the voltage that must be provided by the output circuit in order to produce a given output current in the total load. This can be minimized by using a large capacitance value component, but such capacitors are physically bulky and one is required for each intracochlear electrode contact.

In order to save space in some cases, blocking capacitors have been omitted in favor of a passive discharge scheme which assumes that any residual charge will be trapped by and produce a small polarization of the intrinsic capacitance of the metal-electrolyte interface, which polarization can be bled off the capacitance by shorting the electrode pair together between pulses. The maximal permissible polarization that can accumulate safely on the metal-electrolyte interface is limited by the electromotive force required for the electrolysis of the saline body fluids, which is about ±0.8 VDC, a value that is far lower than the compliance voltage actually available to the electronic circuitry (±5 to ±15 VDC). Thus, the stimulus-generating circuitry can easily produce conditions that are known to lead to electrolytic damage to both the electrodes and the surrounding tissue.

3. Prevention of Shunts Between Leads

Each of the intracochlear contacts generally requires a separate insulated wire from the stimulus generating circuitry to the contact itself. These fine wires must be bundled closely together in a highly flexible cable and they often sustain substantial handling during fabrication of the electrode array and cable. Because the electrodes themselves have substantial impedance, even small leaks in the insulation between individual wires and between a wire and the conductive body fluids surrounding the lead and the electrode may result in substantial shunting of output current away from the desired electrode contact, thereby degrading performance.

4. Prevention of Shunts Between Feedthroughs

The electronic circuitry is usually sealed into an enclosure made of ceramic and/or metal with hermetically sealed feedthroughs to each of the leads going to each of the electrodes. In order to minimize the size of the case, it is desirable to make these multiple feedthroughs as small and closely spaced as possible. However, the feedthroughs and the attachments to the wire leads constitutes one of the most vulnerable points for the development of electrical shunts. This is because water vapor that is present in polymeric encapsulants placed over these connection points outside the hermetic package tends to condense on the hydrophilic metal and/or ceramic surfaces of the package and the dielectrics that form part of the feedthrough assemblies. Condensed water tends to dissolve ions from these surfaces and enlarge in volume under osmotic pressure, forming conductive shunts between feedthroughs and leads.

It is thus apparent that there is a need in the art for implantable electrodes for use with an implantable electronic device which facilitate the use of biphasic pulses, prevent the flow of net DC current, and prevent shunts between leads and feedthroughs.

The use of sintered, anodized tantalum as a bioelectrode has been proposed in the prior art (Guyton & Hambrecht, ca 1973), but it has yet to be incorporated into a medical product. A suggestion has been made, see Loeb, et al. (1991, Med. & Biol. Engng. & Comput. 29:NS13–19) to use such electrodes to store the energy for stimulation pulses in an electrolytic capacitor formed by sintered, anodized tantalum in series with saline body fluids and a counterelectrode made of iridium with an electrochemically activated surface. See also , U.S. Pat. Nos. 5,193,539; 5,193,540; 5,312,439; 5,324,316 and 5,405,367, which patents are incorporated herein by reference. The combination electrodes described in these references is particularly useful for the generation of monophasic pulses because tantalum pentoxide protects against leakage current only as long as it is held at a neutral or anodic potential. Tantalum pentoxide cannot be reverse-biased by more than about 1 volt. Iridium, on the other hand, is equally resistant to corrosion in either polarization. Furthermore, iridium can be electrochemically activated, resulting in a surface layer of iridium oxide that tends to float rapidly to neutral polarization regardless of changes in the polarization of the tantalum pentoxide (Loeb, et al., 1991).

Tantalum metal is a metal of choice for the hermetic feedthroughs and wire leads because tantalum metal is strong, ductile, highly conductive, biocompatible, inexpensive and readily drawn into wire of any desired dimension. It spontaneously forms a native oxide that facilitates hermetic sealing to various glass and ceramic dielectrics commonly employed in hermetic feedthroughs. Use of anodized tantalum feedthroughs and wire leads with non-tantalum electrodes in an implantable electronic tissue stimulator was described by White, 1980 (Annals of Biomed. Engng. 8:317–332).

SUMMARY OF THE INVENTION

The present invention addresses the above and other needs by providing an implant device that uses tantalum and tantalum pentoxide as a complete system for the conveyance of electrical stimulation pulses from stimulus-forming circuitry contained within an hermetic enclosure to the saline fluids of the cochlea (or other tissue to be stimulated).

A preferred application for the present invention is a cochlear prosthesis. Such prosthesis comprises a multiplicity of electrode contacts made from sintered, anodized tantalum, connected via tantalum wire leads to tantalum feedthroughs into an hermetically sealed package containing stimulus pulse-forming electronic circuitry. One or more counterelectrode contacts (for monopolar or bipolar configurations, respectively) are made from activated iridium, connected via platinum or other noble metal leads to noble metal feedthroughs. When powered-up, the stimulus generating circuit produces a steady polarizing potential of approximately half its maximum output voltage range, which potential is applied as a positive (anodizing) voltage to each tantalum electrode and associated lead and feedthrough, with respect to the activated iridium electrode (s), which act as the reference point for the circuit.

In accordance with one aspect, the present invention advantageously eliminates the need for internal coupling capacitors without the usual danger of having DC current flow to the saline fluids. Further, the present invention eliminates the need for high integrity and adhesion in other dielectrics used to encapsulate the feedthroughs and wires outside the hermetic package en route to the cochlea (or other stimulation site).

When used with a counterelectrode made of activated iridium and stimulus-forming circuitry of a type described herein, the present invention increases the power efficiency, the available compliance voltage, and the reliability of such stimulus-forming circuitry. Moreover, the present invention simplifies the fabrication and improves the reliability of the electrode array and associated flexible cable connecting the array to the stimulus-forming circuitry.

It is thus an object of the present invention to provide an electrical implant device that avoids the use of coupling capacitors, yet eliminates the danger of applying DC current to saline fluids/tissue.

It is a further object of the invention to provide implantable electrodes, or an implantable electrode array, that employs tantalum metal.

It is another object of the invention, in accordance with one embodiment thereof, to provide an implantable stimulation device wherein tantalum and tantalum pentoxide combine to provide a complete system for the conveyance of electrical stimulation pulses from hermetically sealed stimulus-forming circuitry to the saline fluids/tissue to be stimulated.

It is a feature of the invention to reduce the cost, simplify the design, and improve the reliability of implantable electronic devices, including implantable electrode arrays.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The general design of a cochlear prosthesis made in accordance with the present invention comprises of a multiplicity of electrode contacts made from sintered, anodized tantalum, connected via tantalum wire leads to tantalum feedthroughs into the hermetically sealed package containing the stimulus pulse-forming electronic circuitry. One or more counterelectrode contacts (for monopolar or bipolar configurations, respectively) consist of activated iridium, connected via platinum or other noble metal leads to noble metal feedthroughs. When powered-up, the stimulus generating circuit produces a steady polarizing potential of approximately half its maximum output voltage range, which potential is applied as a positive (anodizing) voltage to each tantalum electrode and associated lead and feedthrough, with respect to the activated iridium electrode (s), which act as the reference point for the circuit. This powering-up process must be conducted slowly enough so that the currents required for the build-up of charge on the Ta electrodes do not produce undesirable stimulation or electrochemical effects; similarly, the powering-down process of discharging the Ta electrodes must be well-controlled. Stimulus pulses or other desired biphasic waveforms are produced by driving each tantalum electrode more or less positive than this nominal steady polarizing potential.

The available capacitance of the sintered, anodized Ta electrode needs to produce a reactance to the applied current that is small compared to the rest of the impedance of the load, which consists largely of the resistance of the surrounding saline-filled tissues. Based on experience, a capacitance of about 0.1–1.0 $\mu$F should be readily attainable, which would produce a reactance of less than 1 k$\Omega$ compared to the tissue resistance of about 10 k$\Omega$. The steady anodizing potential applied to the tantalum components tends to reinforce the previously applied anodization layer, limiting to a nominal value the amount of DC that can be applied even in the event of a failure of the circuitry or a defect in the anodization layer. In fact, portions of the tantalum leads that are generally well-covered by other dielectrics do not need to be anodized prior to use because the prolonged presence of the anodizing polarization voltage will eventually cause any small regions of exposed tantalum to become anodized. The cathodic potential applied to the iridium electrode is absorbed by valence shifts within the activated iridium layer, as described by Loeb, et al. (1991).

Figure 1A:
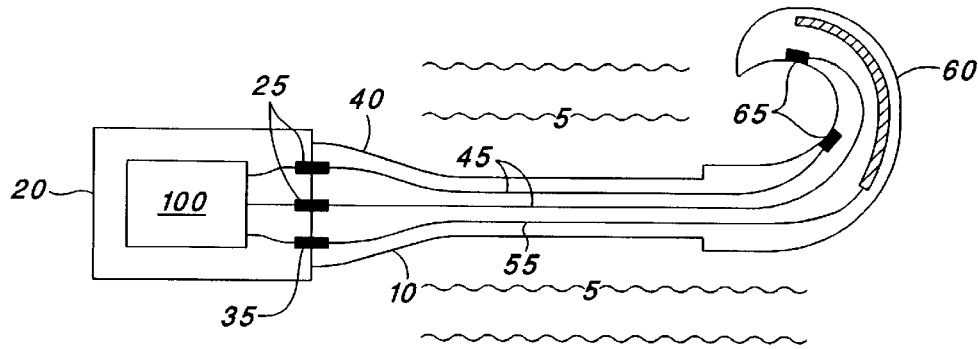
FIGS. 1A–1D diagrammatically depict various electrode arrays made in accordance with the present invention.
Figure 1B:
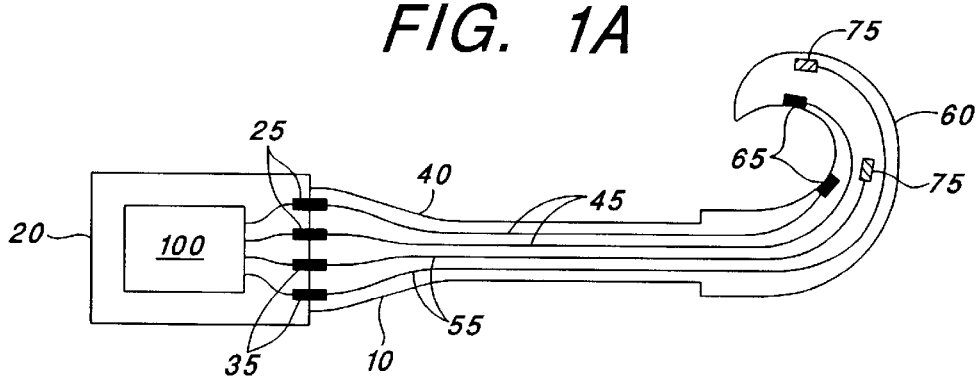
Figure 1C:
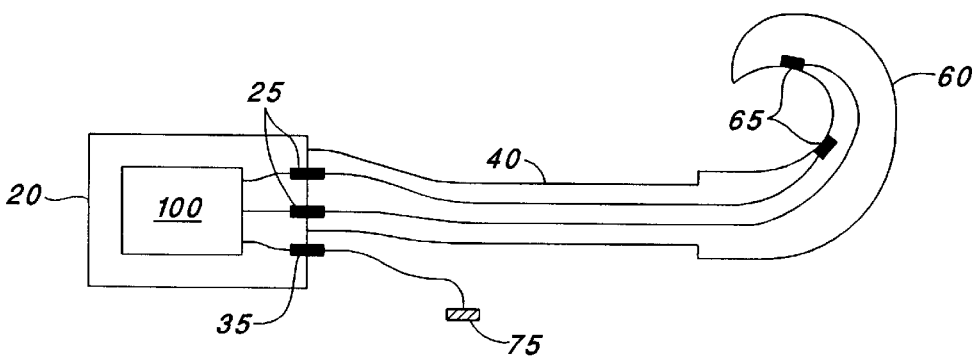
Figure 1D:
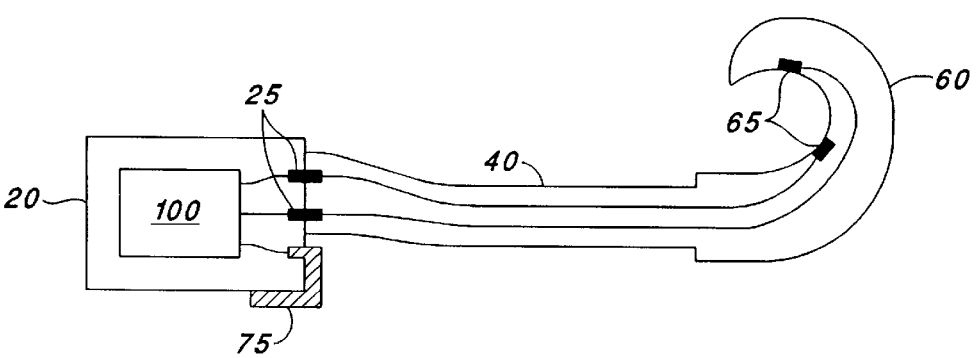
Figure 1E:
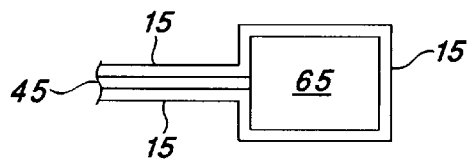
FIG. 1E shows an enlarged view of a tantalum electrode used in the embodiments of the invention shown in FIGS. 1A–1D, and illustrate the formation of a tantalum pentoxide layer on the electrode.

As shown in FIG. 1A, the implanted portions of the cochlear prosthesis comprise an hermetically sealed enclosure 20 containing stimulus pulse-generating circuitry 100. A flexible cable 40 contains electrical leads 45 that connect the circuitry 100, via feedthroughs 25, to an intracochlear electrode array 60, all disposed in saline fluids 5 of the body tissues in which these portions are surgically implanted. The intracochlear electrode array 60 contains a multiplicity of sintered, anodized tantalum electrode contacts 65, each connected via an anodized tantalum lead 45 to an anodized tantalum feedthrough 25 that passes through and is hermetically sealed to the enclosure 20. One or more iridium counterelectrodes 75 may be disposed within the electrode array 60 as shown in FIG. 1A and FIG. 1B. Alternatively, or additionally, as shown in FIG. 1C or 1D, one or more iridium counterelectrodes 75 may be located outside of the electrode array 60. Each such iridium counterelectrode 75 is connected via a noble metal conductor 55 to a noble metal feedthrough 35 of the enclosure 20. If it is desired to have the counterelectrode 75 located in a particular manner within the cochlear array as shown in FIG. 1A, or if more than one counterelectrode 75 is employed as shown in FIG. B, then the corresponding conductor(s) 55 and feedthroughs 35 should be insulated with a conventional dielectric coating 10 such as silicone elastomer or Teflon. The anodized tantalum components 25, 45 and 65 require no additional insulation beyond the electrochemically grown layer of tantalum pentoxide 15 (FIG. 1E) that is formed on their surfaces during manufacture or during use. However, the application of dielectric coatings, encapsulates or moldings 10 may be desirable to limit the passage of alternating current from stimulation pulses between the tantalum conductors and into any surrounding saline fluids as a result of stray capacitance through the tantalum pentoxide 15. Generally, some such coatings, encapsulates or moldings 10 will be employed to provide mechanical strain relief for the connection of wire leads to feedthroughs and to give the desired physical shape and handling properties to the electrode array 60 and flexible cable 40.

Figure 2:
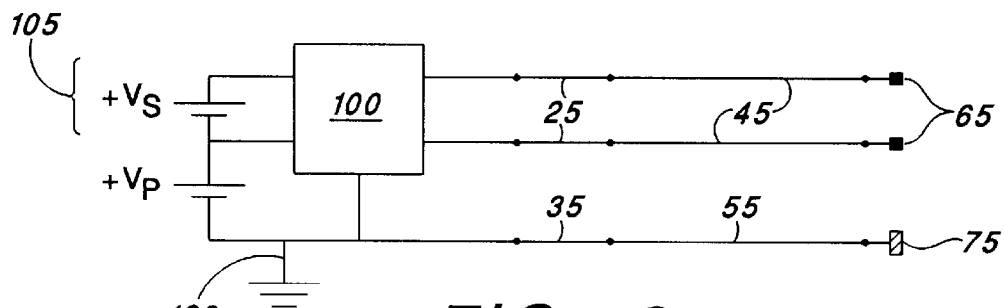
FIG. 2 is a block diagram illustrating how the electrodes of the invention are used with stimulus-forming circuitry.
Figure 3A:
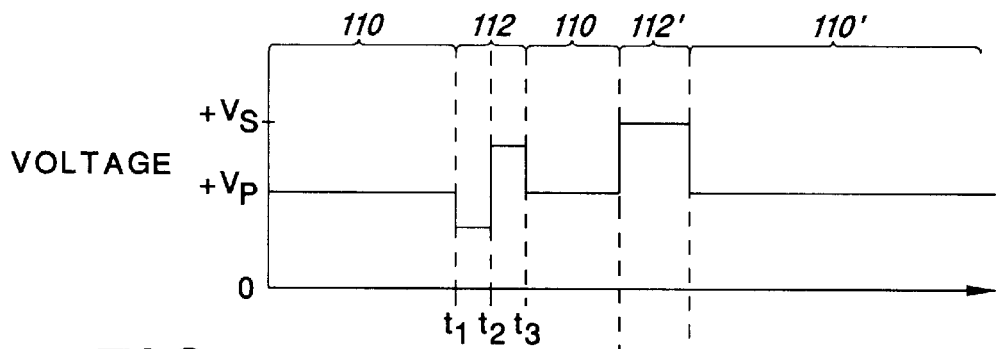
FIGS. 3A and 3B are timing diagrams that illustrate the voltage and current, respectively, associated with the use of the electrodes and stimulus-forming circuitry of FIG. 2.
Figure 3B:
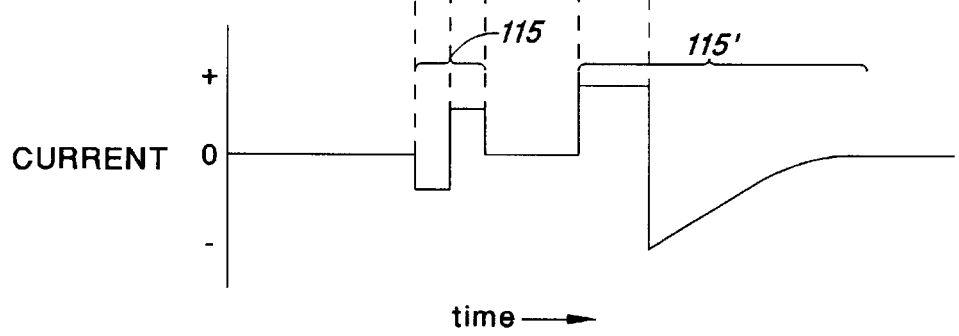

As shown in the timing diagrams of FIGS. 3A and 3B, the electrical circuitry 100 applies a steady anodic polarization +Vp during periods 110 to each tantalum feedthrough 25 and its connected tantalum wire 45 and tantalum electrode contact 65, with respect to the reference point (e.g., ground reference) 120 (FIG. 2) of the circuit which is connected to the noble metal feedthrough(s) 35 and thence to any iridium counterelectrode(s) 75. This steady anodic polarization during the period 110 is approximately half of the available power supply voltage (sum of +Vp plus +Vs) 105 that is available in the electrical circuitry 100. When the application of stimulating current to the electrode array is desired, during time 115 (FIG. 3B), the electrical circuitry 100 produces a sequence of potential changes during time 112 (FIG. 3A) in the potential applied to the particular electrode contacts through which the stimulating current is desired to flow. The electrode contacts 65 must always be stimulated as pairings in which one or more contacts are connected so as to form one half of the pair, all of which contacts must be anodized tantalum electrode contacts 65, and one or more contacts are connected so as to form the other half of the pair, all of which contacts must be activated iridium contacts 75. When further stimulating current is no longer desired, the sequence of potential variations or changes about the polarization voltage +Vp (during time period 112) is terminated, with a return to the steady anodic polarization +Vp during period 110.

Because the anodized tantalum surfaces comprising one half of the pairing act like capacitors with very low DC leakage, only charge-balanced alternating current can pass through the saline fluids 5 regardless of the potentials applied to these electrodes. If the sequence of voltage variations or changes does not itself result in no net charge flow in either direction, as shown, e.g., at time 112' (FIG. 3A), then the return to the steady anodic polarization +Vp during time 110' results in discharge of the charge stored temporarily in this capacitance, resulting in a current waveform such as shown at time 115' in FIG. 3B.

All activated iridium contacts 75 are connected to the reference point 120 of the electronic circuitry 100, which operates with only one polarity of voltages +Vs and +Vp (105) in its power supply. Thus, the electronic stimulus-forming circuitry 100 is not capable of causing net direct current to flow through the activated iridium contacts 75.

Thus, in operation, it is seen from FIGS. 2, 3A and 3B that the stimulus-forming circuitry derives a source of operating potential Vs, which it uses as a source of power within the stimulus-forming electronic circuitry. There is also included within, or coupled to, the stimulus-forming circuitry 100 a means for maintaining an anodic voltage +Vp between the tantalum feedthrough(s) 25 and the noble metal feedthrough 35, with the tantalum feedthrough being positive relative to the noble metal feedthrough. Any suitable means may be used for maintaining or applying this anodic voltage +Vp between the feedthrough(s) 25 and feedthrough 35, as is known in the art. Note that the anodic voltage +Vp is generally no greater than about ½ of the operating potential Vs.

When a biphasic stimulation current pulse is desired, the voltage that is applied between the tantalum feedthrough(s) 25 and the noble metal feedthrough 35 by the stimulus-forming circuitry 100 is varied by an amount ±Δ, where the voltage amount Δ is that amount required to cause the desired stimulating current to flow through electrode 65, but keeping such applied voltage within the range of zero to the sum of +Vp and +Vs. That is, as seen best in FIGS. 3A and 3B, the voltage appearing across the tantalum feedthrough (s) 25 and the noble metal feedthrough 35 comprises a voltage +Vp−Δ for a period of time from t1 to t2, followed by a voltage +Vp+Δ for the period of time t2 to t3. It is generally preferred that the time period t1–t2 be the same as the time period t2–t3 so that the resulting biphasic current pulse is balanced. Of course, balancing may still be achieved even if the time periods t1–t2 and t2–t3 are not equal simply by adjusting the amplitudes of the respective negative or positive halves of the biphasic pulse.

It should also be noted that while it is generally preferred that the first half of the biphasic pulse be negative, as shown in FIG. 3B, such is not mandated by the present invention. It is possible to have the biphasic pulse be positive for the first half, followed by the negative pulse. What is important for purposes of the present invention is that the voltage appearing across the tantalum feedthrough(s) 25 and the noble metal feedthrough 35 be varied or changed so that it comprises a voltage +Vp±Δ for a period of time from t1 to t2, followed by a voltage +Vp±Δ for the period of time t2 to t3 so that a balanced biphasic current pulse will flow during the time period t1 to t3 (112) through the saline liquids and tissue adjacent the tantalum electrode(s) 65 and the iridium counterelectrode 75.

It should further be noted that the cochlear electrode array and associated stimulation circuitry that are the subject of the present invention can also be used to generate more complex stimulus waveforms having multiple or even continuous phases, subject only to the limitation imposed by the capacitive coupling that prevents creating waveforms with a net direct current flow in either direction.

Figure 4:
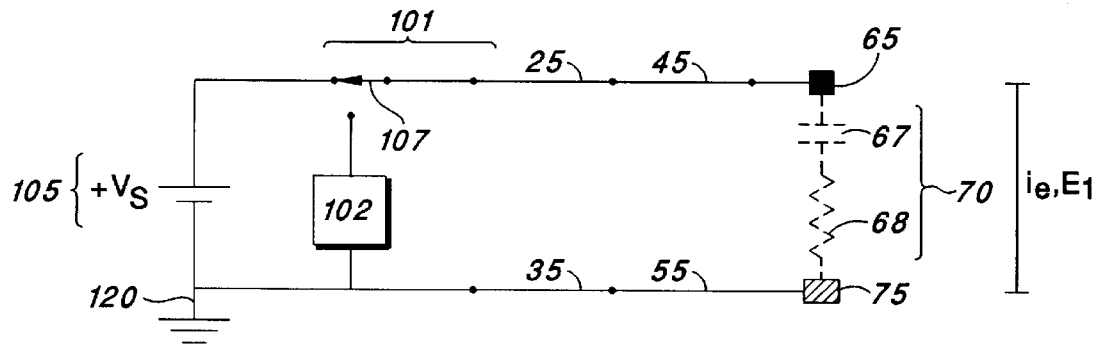
FIG. 4 shows alternative stimulation circuitry that may be used in accordance with the invention when only biphasic stimulation pulses are desired.
Figure 5A:
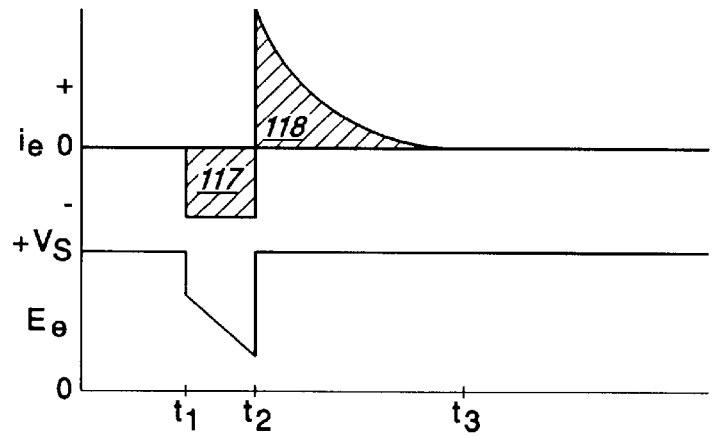
FIGS. 5A and 5B show current and voltage waveforms associated with the operation of the circuit of FIG. 4.

In the event that only biphasic stimulation pulses are desired, the cochlear electrode array that is a part of the present invention can be used advantageously with alternative stimulation circuitry 101 shown in FIG. 4. The alternative stimulation circuitry 101, when used in conjunction with an electrode array of the type herein described, produces only biphasic pulses of the form shown in FIGS. 5A and 5B, in which the first phase 117 of the pulse applied by tantalum electrode 65 is cathodal (i.e., positively charged current flows toward the active tantalum electrode 65 from the reference iridium electrode 75). This polarity of biphasic pulsing is known to be more effective for stimulating excitable tissues that are physically close to the electrode contact whose first phase is cathodal. It is also a property of this circuitry that the shapes of the successive cathodal phase 117 and anodal phase 118 are not necessarily symmetrical but that the total charge delivered (which is the area under the curve in the current vs. time traces $i_e$ in FIGS. 5A and 5B) is equal and opposite in the two successive phases 117 and 118.

Circuit 101 operates in conjunction with a single power supply 105 which is normally connected via switch 107 to tantalum electrode 65 so as to polarize potential Ee to the maximal positive voltage +Vs. Electrodes 65 and 75 and the intervening body fluids have an approximately equivalent circuit 70 composed of the series combination of electrolytic capacitance 67 and resistance 68. When a stimulation pulse is desired, switch 107 is connected for the duration of the first, cathodal phase 117 of the stimulation pulse to a stimulus control circuit 102. At the end of cathodal phase 117, switch 107 reconnects electrode 65 to power supply 105, causing anodal current 118 to flow as capacitance 67 is repolarized to the value +Vs. Because of capacitance 67, the charge transferred during cathodal phase 117 must be equal and opposite to that transferred during anodal phase 118.

In one alternative embodiment, stimulus control circuit 102 may perform the function of permitting a regulated current to flow. In that case, the strength of the stimulation pulse is determined by controlling the amplitude and duration of the current. This results in the waveforms of electrode current $i_e$ and potential Ee shown in FIG. 5A. During cathodal phase 117, which lasts from t1 to t2, circuit 102 pulls potential Ee progressively lower in order to maintain constant current flow as capacitance 67 is discharged. During anodal phase 118, from t2 to t3, the current $i_e$ varies exponentially according to the time constant determined by capacitance 67, resistance 68 and any internal resistance of other conductors and power supplies in the circuit.

Figure 5B:
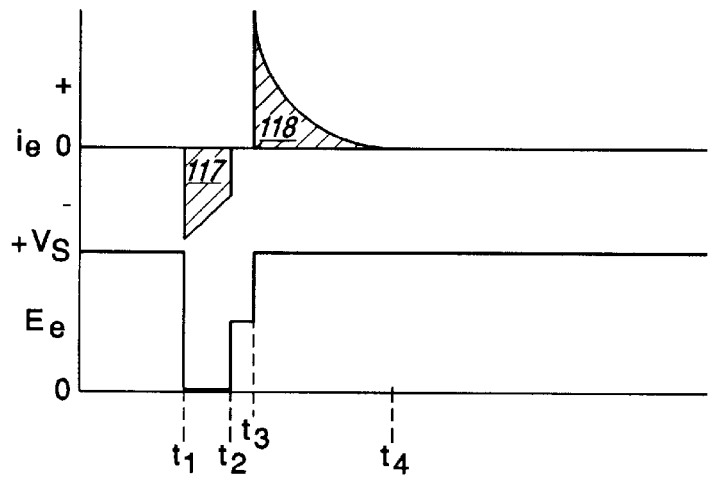

Alternatively, the strength of a stimulation pulse may be determined by controlling the total charge of its cathodal phase 117, without explicitly controlling either the current or the duration. FIG. 5B shows one possible set of waveforms of the electrode current $i_e$ and potential Ee that can be generated in this manner. During cathodal phase 117, from t1 to t2, circuit 102 effectively short-circuits tantalum electrode 65 to reference electrode 75, causing Ee to fall to zero. Current $i_e$ flows according to the time constant determined by capacitance 67, resistance 68 and any internal resistances. After the required cathodal charge has flowed, from time t2 to t3, circuit 102 goes into an open state in which no current flows, during which Ee represents the residual charge remaining on capacitance 67. Anodal phase 118 is produced by reconnecting electrode 65 to power supply 105. This method of controlling stimulus intensity by metering charge instead of current has the advantage of eliminating the dissipation of power that normally occurs in current-regulating circuits. It generates the shortest possible duration of cathodal pulse that can be produced given the available power supply voltage +Vs and impedance of equivalent circuit 70. It permits a delay interval between the cathodal and anodal pulses, which is known to improve the efficiency of the neural response to electrical stimulation with brief, biphasic pulses.

Figure 6A:
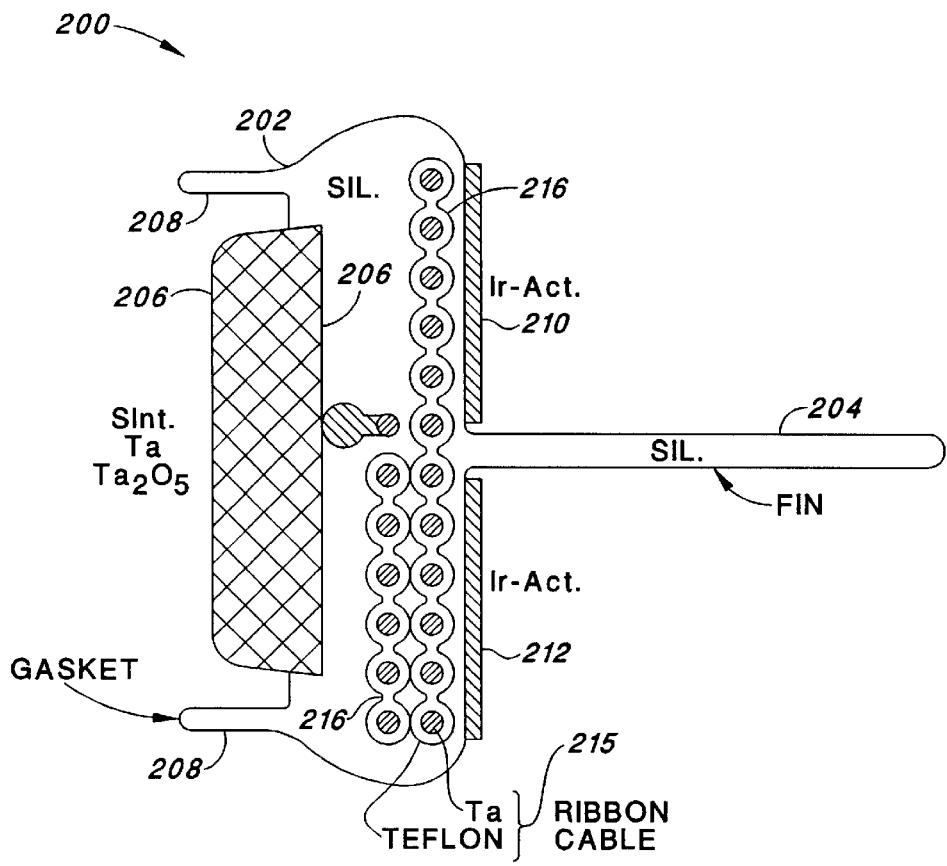
FIG. 6A shows a radial cross sectional-view of an electrode array made in accordance with the invention, with the view being made near the base of the array.
Figure 6B:
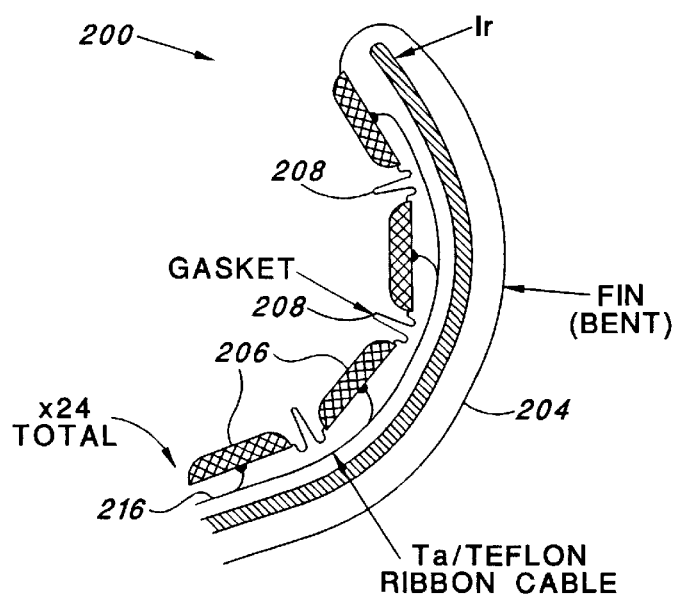
FIG. 6B shows a longitudinal cross-sectional view of the electrode array of FIG. 4A, with the view being taken near the apex of the array.

Turning next to FIGS. 6A and 6B, details are shown of a more complete and explicit design for a cochlear electrode array 200 that incorporates several features of the present invention plus additional features of inventions disclosed in pending patent applications. For example, reference is made to U.S. patent application Ser. No. 08/516,758, filed Aug.18, 1995, and U.S. patent application Ser. No. 08/447,455, filed May 23, 1995, both of which patent applications are incorporated herein by reference, which disclose various features of electrodes and electrode arrays for use with implantable stimulation devices. FIG. 6A shows a transverse cross sectional-view of the electrode array 200 with the sectional view being made near the base of the array. FIG. 6B shows a longitudinal cross-sectional view of the electrode array 200, with the sectional view being taken near the apex of the array.

As seen in FIGS. 6A and 6B, the array 200 is preferably made from a silicone molding 202 with a complex cross-section and a performed spiral shape that is designed to optimally position a set of 24 sintered Ta contacts 206 at regular intervals of about 0.8 mm over most of the 24 mm length of the array. Each contact faces the medial wall of the scala tympani and is surrounded by a very thin, deformable ring 208 of molded silicone that acts like a gasket to force its stimulating current into the bone overlying the spiral ganglion cells. These contacts and gaskets are forced against the medial wall by the combined pull of the springy spiral shape and the push of a longitudinally disposed fin 204 directed toward the lateral wall.

Two elongated common electrodes 210, 212 are shown above and below the horizontal meridian and facing laterally. One or the other of these electrodes 210 or 212 would be electronically switched to the reference point 120 of the circuitry to act as the return electrode in a bipolar edge-effect array as described in the '758 patent application referenced above. Note that the edge-to-edge distance of the Ir to adjacent Ta electrodes is, in fact, short enough to produce the desired bipolar focusing based on edge-effects, even though the contacts actually face in opposite directions. The upper Ir common electrode 210 would be most useful when stimulating spiral ganglion cells with a high rate of apical dendrite survival because it would produce current flow through the habenula perforata in which such dendrites lie. The lower Ir common electrode 212 would be most useful when stimulating spiral ganglion cell bodies directly, as these lie mostly below the horizontal meridian, with axonal processes projecting downward into the modiolar bone. Note that because of the resting polarization of the Ta at a potential of +Vp, (approximately half the operating voltage range) it is possible to apply either anodal-first or cathodal-first biphasic pulses in either bipolar configuration.

Note further that all of the rigid elements are oriented vertically and stacked in as narrow a space as possible to facilitate flexing of the electrode only in the axis of the spiral during insertion. In particular, the 24 Ta leads connecting to each of the 24 Ta electrodes are organized into two 12-conductor ribbon cables 215, each consisting of 12 0.001" Ta conductors held on 0.003" centers by a Teflon extrusion 216. Individual leads from these ribbon cables are stripped of the Teflon carrier 216 by a highly focused laser, which melts the end of the Ta wire into a small ball and welds it to the sintered Ta electrode contact 206. It is important to make such connections without contacting the Ta parts with another metal (such as might be employed in resistance welding electrodes), because metallic impurities in the Ta may interfere with the formation of a leak-free anodization layer.

In one possible sequence of manufacture, the Ta leads would be similarly laser welded to the Ta feedthroughs 25 on the hermetic package and the subassembly of Ta contacts. The ribbon cables 215 and feedthroughs 25 would then be anodized to about 4 times the maximum anticipated working voltage (the sum of +Vp plus +Vs) to provide a leak-free anodization layer. This subassembly would then be placed in the mold along with the ribbon-shaped Ir common electrodes 210, 212. A single injection process would simultaneously form the silicone material comprising the electrode carrier 216, the flexible lead cable 45 and the strain-relief 40 over the feedthroughs 25. Note that any voids or defects in the Teflon of the ribbon cable or the silicone material would be inconsequential sources of shunts because of the prior or eventual anodization of all potentially exposed Ta surfaces. Any shunts relative to the Ir electrodes 210, 212, their noble metal leads 55 and feedthroughs 35 would also be inconsequential because of the principle of the edge-effect electrode, in which only the region of the common electrode surface that is immediately adjacent to the active electrode actually carries any significant amount of current.

While the invention herein disclosed has been described by means of specific embodiments and applications thereof, numerous modifications and variations could be made thereto by those skilled in the art without departing from the scope of the invention set forth in the claims.

What is claimed is:

1. An implantable tissue-stimulating prosthesis comprising implantable stimulus-forming electronic circuitry hermetically sealed in a package, said package comprising a tantalum feedthrough which provides an electrical path to the stimulus-forming circuitry hermetically sealed within said package, and a noble metal feedthrough that provides a return electrical path to the stimulus-forming circuitry hermetically sealed within said package;

at least one electrode contact made from sintered, anodized tantalum;

at least one tantalum wire lead connecting a respective at least one electrode contact to the tantalum feedthrough, whereby the electrode contact is electrically connected to the tantalum feedthrough, and hence to the stimulus-forming electronic circuitry;

a layer of tantalum pentoxide covering said tantalum electrode contact and at least those portions of said tantalum wire lead that are exposed to body fluids;

a counterelectrode contact made from activated iridium; and a noble metal lead connecting the counterelectrode to the noble metal feedthrough;

wherein the implanted stimulus-forming electronic circuitry comprises means for deriving a source of operating potential $V_s$, means for maintaining an anodic voltage +Vp between the tantalum feedthrough and the noble metal feedthrough, with the tantalum feedthrough being positive relative to the noble metal feedthrough, the anodic voltage +Vp being no greater than about ½ of the operating potential $V_s$, and means for varying the voltage that is applied between the tantalum feedthrough and the noble metal feedthrough by an amount ±Δ so as to cause a balanced biphasic current pulse to flow between the tantalum electrode and the iridium counterelectrode.

2. An implantable tissue-stimulating prosthesis comprising implanted stimulus-forming electronic circuitry hermetically sealed in a package, said package including a plurality of tantalum feedthroughs which provide an electrical path to the stimulus-forming circuitry hermetically sealed in said package, and at least one noble metal feedthrough that provides a return electrical path to the stimulus-forming circuitry hermetically sealed in said package;

a plurality of electrode contacts made from sintered, anodized tantalum;

a plurality of tantalum wire leads, each connecting one of the plurality of electrode contacts to a respective one of the plurality of tantalum feedthroughs, whereby each of the plurality of electrode contacts is electrically connected to one of the plurality of tantalum feedthroughs;

at least one counterelectrode contact made from activated iridium; and at least one lead made from a noble metal connecting the at least one counterelectrode to the at least one noble metal feedthrough;

wherein said implanted stimulus-forming electronic circuitry comprises:

means for deriving a single source of operating potential $V_s$ and applying said potential $V_s$ to maintain an anodic polarization between the tantalum feedthrough and the noble metal feedthrough when stimulation is not desired, and means for generating a biphasic stimulus between a selected one of said anodized tantalum electrode contacts and said at least one counterelectrode when stimulation is desired, including means for controlling a cathodal phase of the biphasic stimulus by discharging electrical charge stored by a capacitance formed by said anodized tantalum electrode contact, said activated iridium electrode contact and intervening tissues and fluids.

3. The implantable tissue-stimulating prosthesis as set forth in claim 2 wherein said means for controlling the cathodal phase of a biphasic pulse produces an approximately constant flow of current having a predetermined magnitude for a predetermined period of time.

4. The implantable tissue-stimulating prosthesis as set forth in claim 2 wherein said means for controlling the cathodal phase of a biphasic pulse acts as a short circuit until a predetermined amount of charge has flowed.

5. A cochlear prosthesis comprising:

an hermetically sealed package wherein stimulus pulse-forming electronic circuitry is housed;

a multiplicity of tantalum feedthroughs, each of which provides electrical contact with the pulse-forming electronic circuitry within the hermetically sealed package;

a multiplicity of electrode contacts, each electrode contact being connected to a respective one of said multiplicity of tantalum feedthroughs via a respective tantalum wire lead, whereby each electrode contact is electrically connected to the pulse-forming electronic circuitry;

at least one iridium counterelectrode outside of said hermetically sealed package;

at least one noble metal feedthrough connected to said at least one iridium counterelectrode via a respective noble metal lead outside of said hermetically sealed package, and connected to said pulse-forming electronic circuitry within said hermetically sealed package;

potential means within said hermetically sealed package for maintaining a first anodic voltage between each of the multiplicity of tantalum feedthroughs and the at least one noble metal feedthrough, with each tantalum feedthrough being maintained positive relative to the at least one noble metal feedthrough; and means for causing a balanced biphasic current pulse to flow between at least one of the electrodes connected to a respective tantalum feedthrough and the iridium counterelectrode by varying said first anodic voltage by a predetermined amount.

6. The cochlear prosthesis of claim 5 wherein the noble metal lead comprises platinum.

7. The cochlear prosthesis of claim 5 wherein the multiplicity of electrode contacts are connected to the pulse-forming circuitry without the use of any internal coupling capacitors.

* * * * *